US009730678B2

(12) United States Patent
Oldham (10) Patent No.: US 9,730,678 B2
(45) Date of Patent: Aug. 15, 2017

(54) COLLECTING A URINE SAMPLE

(71) Applicant: P1 Technology Limited, Sheffield, South Yorkshire (GB)

(72) Inventor: James Oldham, Sheffield (GB)

(73) Assignee: P1 Technology Ltd., Stocksbridge, Sheffield (GB)

( * ) Notice: Subject to any disclaimer, the term of this patent is extended or adjusted under 35 U.S.C. 154(b) by 76 days.

(21) Appl. No.: 14/560,422

(22) Filed: Dec. 4, 2014

(65) Prior Publication Data
US 2015/0157301 A1    Jun. 11, 2015

(30) Foreign Application Priority Data

Dec. 5, 2013   (GB) .................................. 1321456.4

(51) Int. Cl.
*A61B 10/00*    (2006.01)
(52) U.S. Cl.
CPC .................. *A61B 10/007* (2013.01)
(58) Field of Classification Search
CPC .................................................. A61B 10/007
USPC .................................................. 600/573, 574
See application file for complete search history.

(56) References Cited

U.S. PATENT DOCUMENTS

| 4,040,791 | A | * | 8/1977 | Kuntz | .................. | A61B 10/007 |
| | | | | | | 600/574 |
| 4,494,581 | A | * | 1/1985 | Gordon | ................ | A61B 10/007 |
| | | | | | | 600/574 |
| 7,871,385 | B2 | * | 1/2011 | Levinson | ............. | A61B 10/007 |
| | | | | | | 600/573 |

FOREIGN PATENT DOCUMENTS

| GB | 2505701 A | 3/2014 |
| WO | 2005107602 A1 | 11/2005 |

* cited by examiner

*Primary Examiner* — David J McCrosky
(74) *Attorney, Agent, or Firm* — James Creighton Wray; Meera P. Narasimhan (57) ABSTRACT

The collection of a urine sample is disclosed. An inlet receives expelled urine. A first exit (203) directs the expelled urine towards a collection receptacle (202). The collection receptacle cooperates with a valve (201) to close off the receptacle after being filled with an initial flow. A second exit (206) expels excess urine after the receptacle has been filled.

15 Claims, 8 Drawing Sheets

COLLECTING A URINE SAMPLE

CROSS REFERENCE TO RELATED APPLICATIONS

This application claims priority from United Kingdom Patent Application No. 13 21 456.4, filed 5 Dec. 2013, the entire disclosure of which is incorporated herein by reference in its entirety.

BACKGROUND OF THE INVENTION

1. Field of the Invention

The present invention relates to apparatus for collecting expelled urine. The present invention also relates to a method of receiving a sample of urine.

2. Description of the Related Art

It is known to collect urine from patients in order to analyze the urine to identify various diseases. For some diseases, it is appropriate to collect a mid flow of urine, such that an initial flow is rejected, and middle flow of a required amount is collected. Subsequent urine is then rejected.

For other purposes, it is necessary to collect the initial flow of urine. Currently, this is done mechanically by physically holding a receptacle in position so as to collect the initial flow and then moving the receptacle away when urine has been collected.

BRIEF SUMMARY OF THE INVENTION

According to an aspect of the present invention, there is provided an apparatus for collecting expelled urine, comprising: a funnel section for receiving urine and directing said urine to a first exit and a second exit; and a receptacle for receiving and storing urine from said first exit, said receptacle including a substantially spherical floatation valve for closing said receptacle when full, such that said receptacle receives an initial flow of urine and subsequent urine is directed towards said second exit; wherein said substantially spherical floatation valve is configured to engage with said first exit so as to block said first exit and prevent subsequent flow into said first exit after receipt of the initial flow of urine.

In an embodiment, there is provided a deflector for deflecting urine towards said first exit in preference to said second exit.

According to a second aspect of the present invention, there is provided an apparatus for collecting a urine sample, comprising: an inlet for receiving expelled urine; a first exit for directing the received urine towards a collection receptacle, wherein said collection receptacle cooperates with a substantially spherical floatation valve to close off said receptacle after being filled with an initial flow; and a second exit for expelling excess urine after said receptacle has been filled.

In an embodiment, the valve includes a floatation device.

According to a third aspect of the present invention, there is provided a method of receiving a sample of urine, comprising the steps of: placing a substantially spherical floatation valve in a receptacle; attaching said receptacle to a first exit of a collection device, said collection device having a funnel opening and a second exit; directing expelled urine towards said funnel opening such that an initial flow is directed to said receptacle via said opening until said valve closes; engaging said substantially spherical floatation valve with said first exit to block said first exit; and directing subsequent flow to said second exit.

DETAILED DESCRIPTION OF EXAMPLE EMBODIMENTS

FIG. 1

Figure 1:
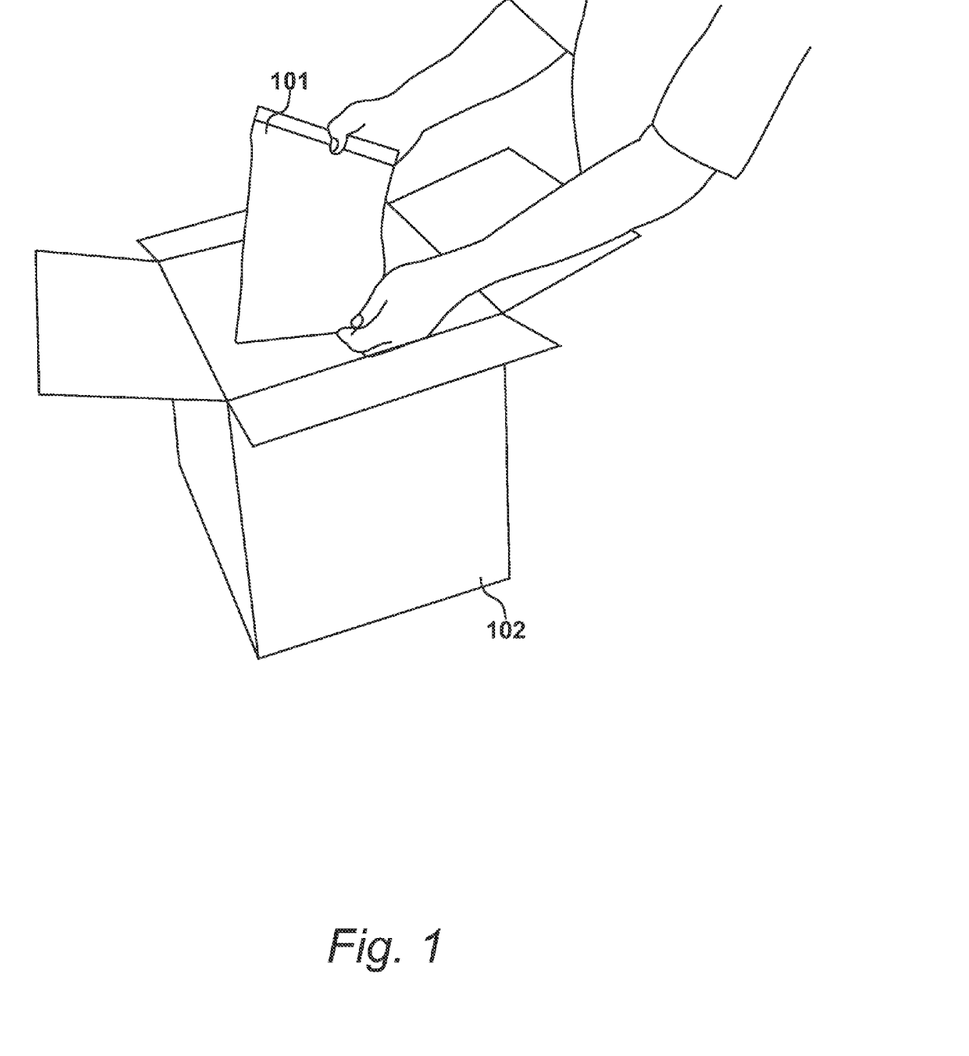
FIG. 1 shows an apparatus for collecting expelled urine.

An apparatus for collecting expelled urine is shown in FIG. 1, contained as a kit of parts 101 and removed from storage 102. The kit of parts includes a funnel section for receiving urine and directing urine to a first exit and to a second exit. It also includes a receptacle for receiving and storing urine from a first exit, including a valve for closing the receptacle when full. In this way, the receptacle receives an initial flow of urine and subsequent urine is directed to the second exit. The kit of parts also includes disposable rubber gloves for a clinician.

FIG. 2

Figure 2:
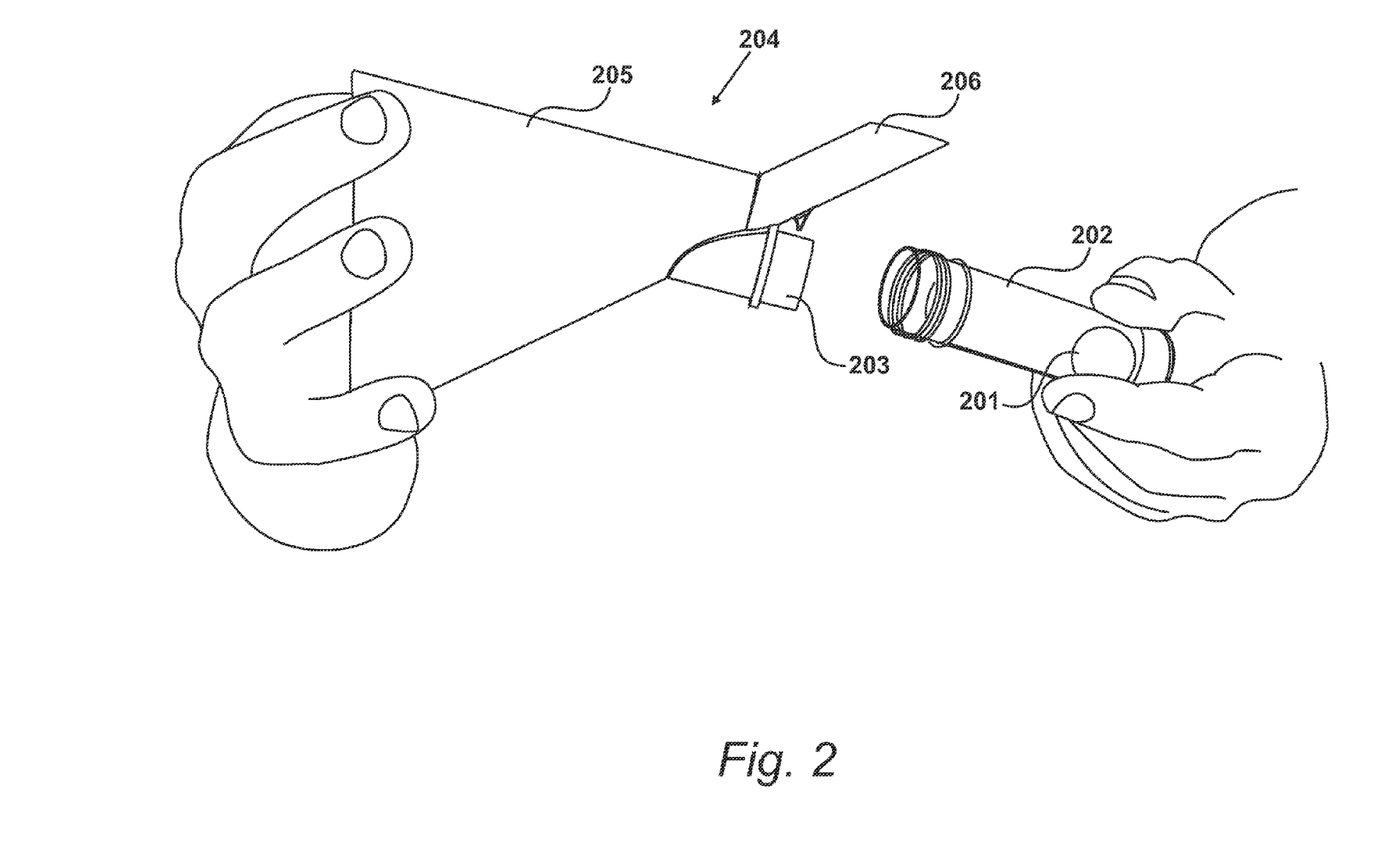
FIG. 2 shows the apparatus of FIG. 1 removed from packaging.

The apparatus identified in FIG. 1 is removed from its packaging, having been produced in sterile conditions. A floatation valve, possibly in the form of a cylindrical hollow ball 201, is placed within a receptacle 202. The receptacle 202 is attached to a first exit 203 of a collecting device 204. The collecting device 204 has a funnel opening 205 and a second exit 206. In use, expelled urine is directed towards the funnel opening such that an initial flow is directed to the receptacle via the first opening until the valve closes. Subsequent flow is then directed towards the second exit.

In this embodiment, the floating device, forming the valve, is substantially spherical. Furthermore, in this embodiment, the spherical valve moves within a substantially cylindrical receptacle.

It should be appreciated that alternative shapes could be deployed for both the receptacle and the valve.

Measures may be taken to adjust the volume of initial flow that is collected. In an embodiment, the spherical valve is replaced with an extended valve such as to take up more space within the container and thereby reduce the amount of urine that may be collected.

In an alternative embodiment, the receptacle could be provided with additional functionality. Thus, chemicals or bio-markers could be included in the receptacle itself. Alternatively, the receptacle could form part of sophisticated equipment for performing an analysis.

FIG. 3

Figure 3:
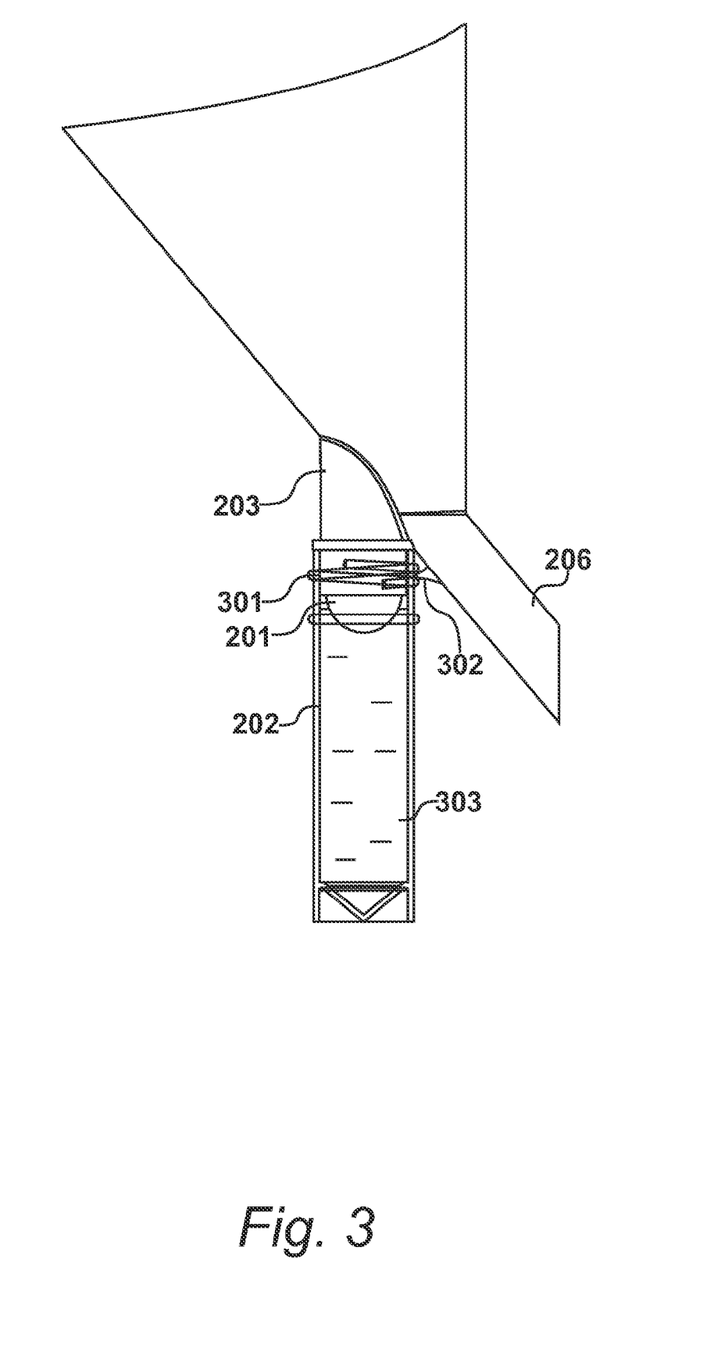
FIG. 3 shows the assembly of the device identified in FIG. 2.

As illustrated in FIG. 3, the receptacle 202 has a screw thread 301. The apparatus is provided with an extending member 302 configured to engage with screw thread 301. In the embodiment shown in FIG. 3, the extending member extends from a side wall of the second exit 206. The receptacle 202, in this embodiment, is substantially cylindrical and the valve comprises a ball 201 configured to float in urine 303 contained within the receptacle.

Thus, in FIG. 2, the ball 201 is shown in its lower position, before urine has been received, and in FIG. 3 the ball 201 is shown in its upper position after urine has been received.

As shown in FIG. 3, after receiving urine, the ball 201 engages with the first exit 203 so as to block the first exit and prevent further flow into receptacle 202.

In an embodiment, the ball 201 is hollow, to facilitate floatation.

In use, after insertion of the floatation valve, in the form of ball 201, expelled urine is directed towards the funnel opening 205 such that an initial flow is directed to the receptacle via the first opening until the valve closes. Subsequent flow is directed towards the second exit. It is therefore possible for the second exit 206 to be arranged such that it directs urine flow to a sanitary system. The second exit is therefore angled, as shown in FIG. 3, such that the receptacle 202 may be held in a substantially vertical orientation, to facilitate the operation of floatation valve 201, with the second exit being directed away from the body, towards a sanitary system.

FIG. 4

Figure 4:
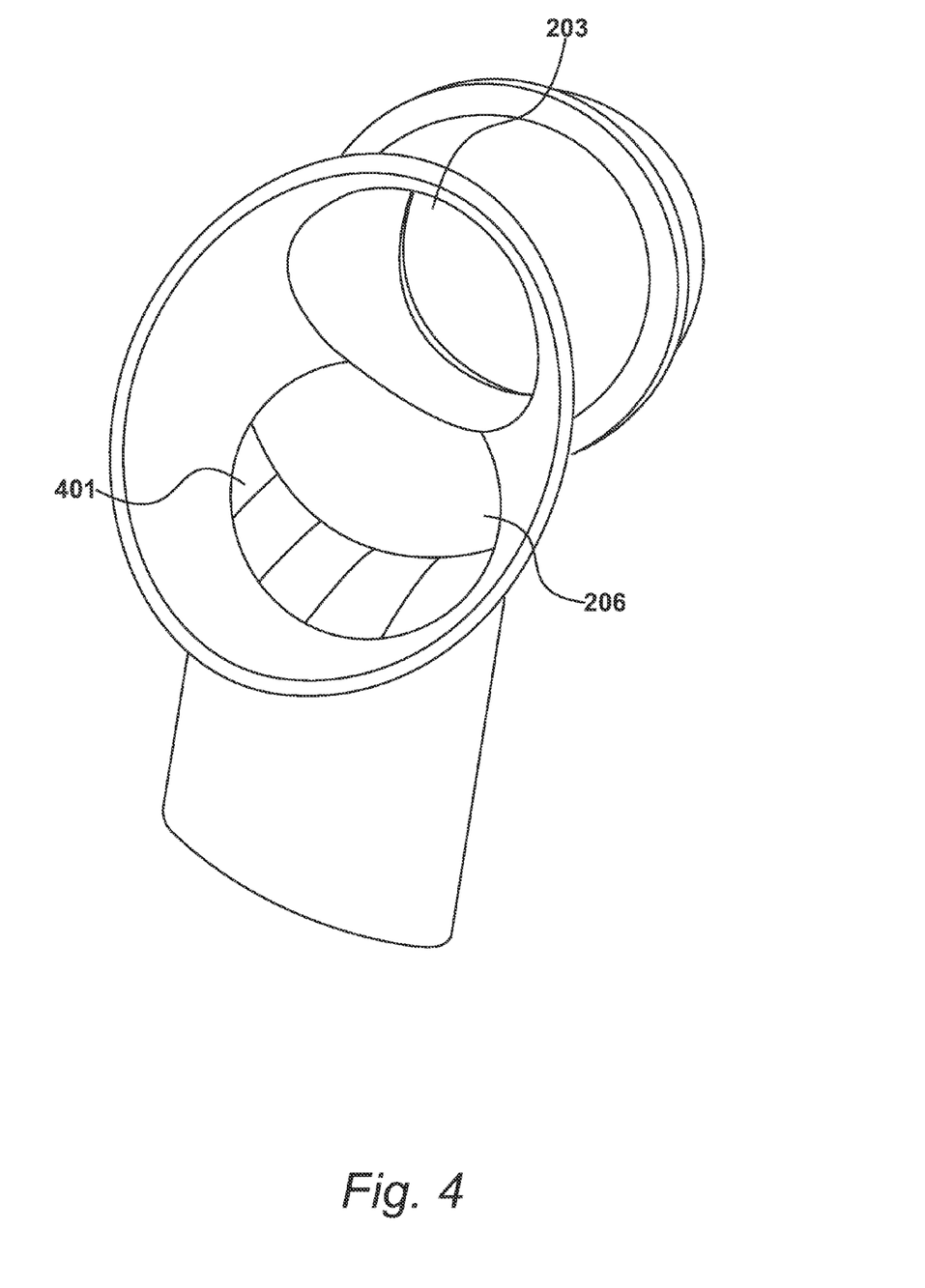
FIG. 4 shows a cross section of the device of FIG. 3.

A cross section of the apparatus for collecting a urine sample is illustrated in FIG. 4. This shows the point at which the apparatus diverges to define a first exit 203 and a second exit 206. In an embodiment, the apparatus includes a deflector 401 configured to deflect urine towards the first exit 203 in preference to the second exit 206. In an embodiment, the apparatus is fabricated from a plastics material by a molding process, therefore it is possible for the deflector 401 to be included as part of the molding. The fabrication of the device in material of this type also facilitates the production of the device as a sterilized item and also facilitates disposal after a single use.

FIG. 5

Figure 5:
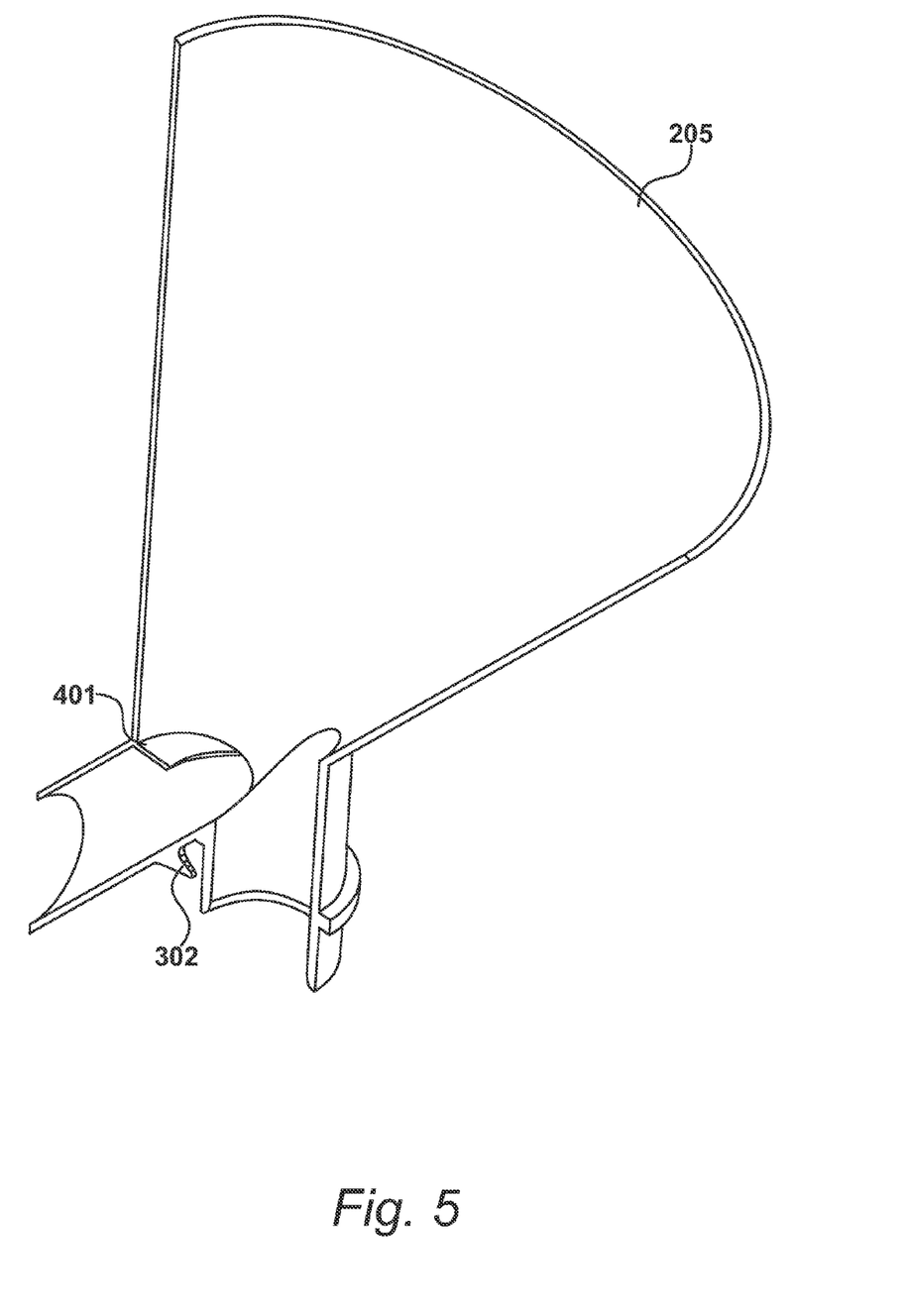
FIG. 5 shows an alternative cross section.

An alternative cross section is shown in FIG. 5, again showing the position of deflector 401. Extending member 302 is also shown in FIG. 5. Inlet 205 is shown, as the inlet for receiving expelled urine. It will be appreciated that alternative configurations could be deployed for inlet 205, in order to accommodate alternative forms of application.

FIG. 6

Figure 6:
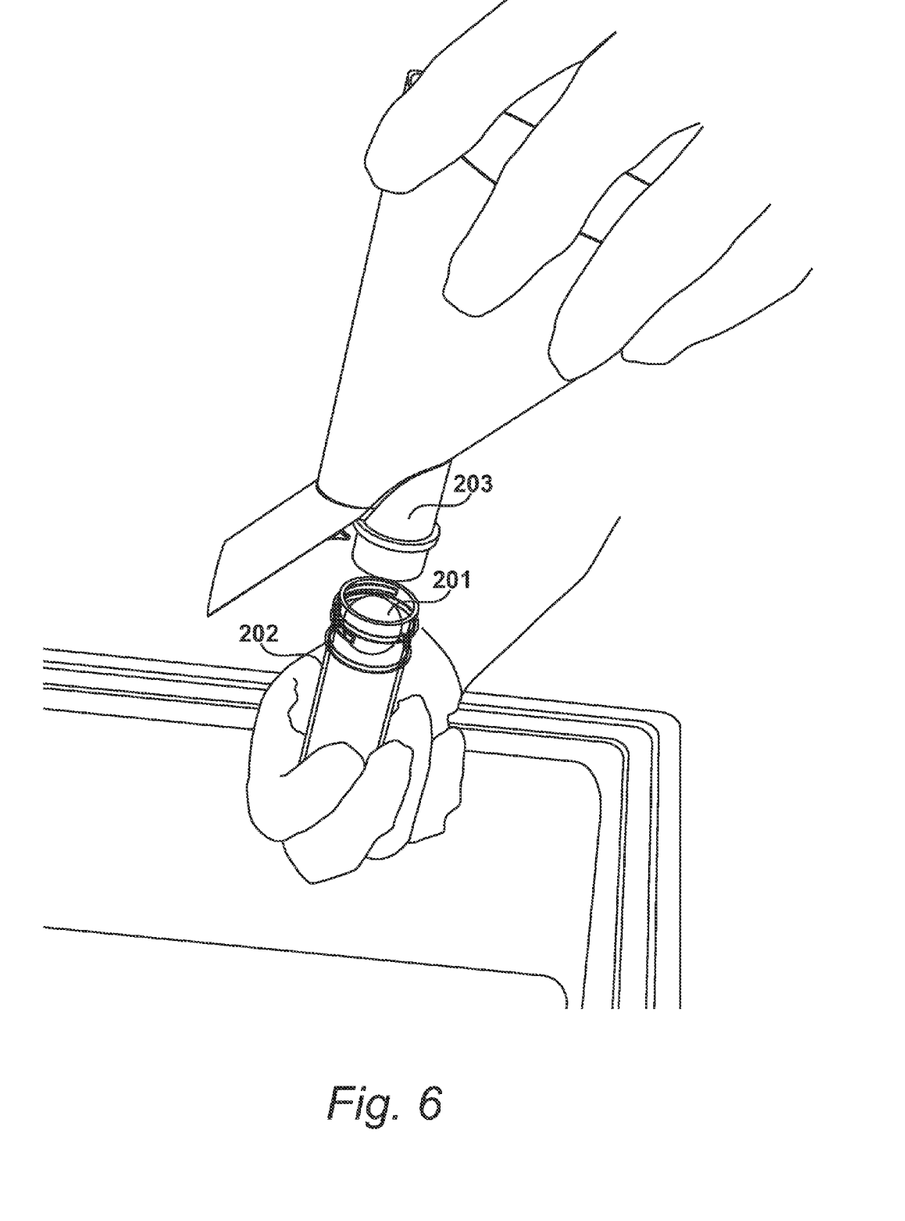
FIG. 6 shows the apparatus after use.

After using the apparatus in order to fill container 202 with an initial flow, the apparatus is returned to the clinician. In clean conditions, container 202 is unscrewed from the first exit 203 and in this embodiment, the spherical floatation valve 201 may remain in place.

FIG. 7

Figure 7:
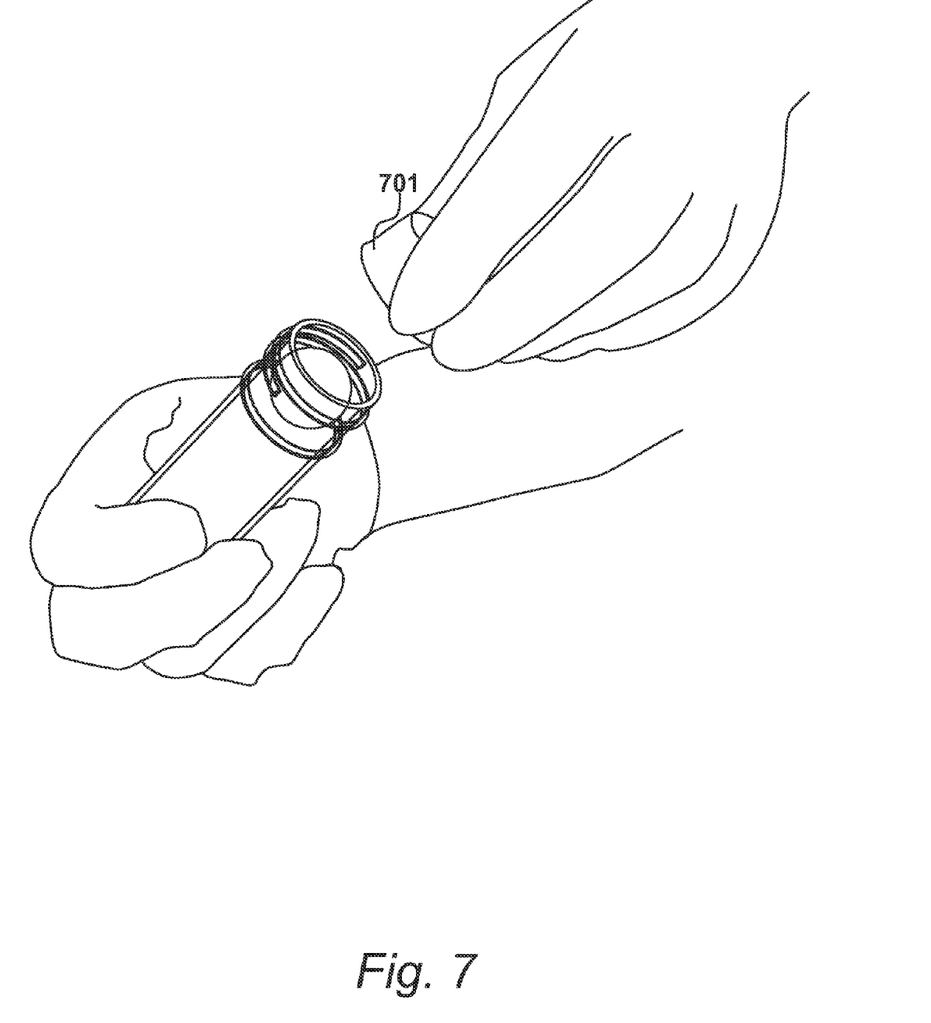
FIG. 7 shows the sealing of the receptacle.

After the receptacle has been unscrewed, a cap 701 is used to seal the receptacle 202 and the container 202 may be labeled with appropriate patient details.

FIG. 8

Figure 8:
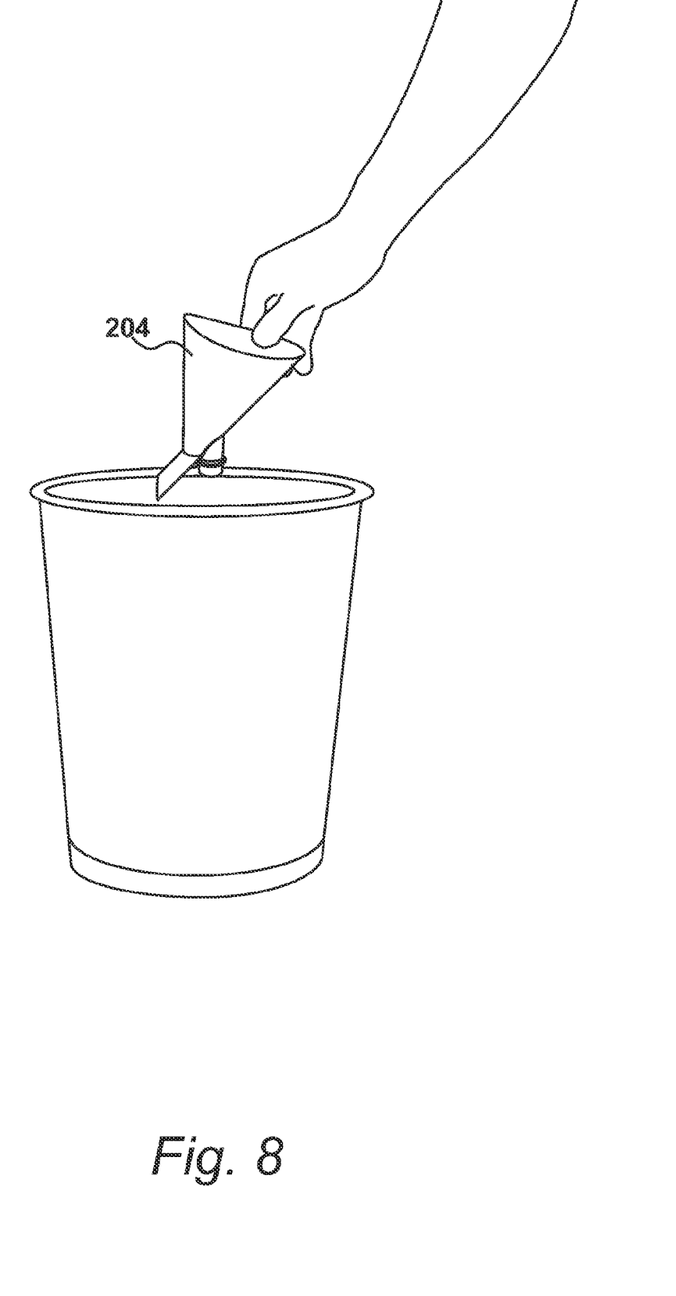
FIG. 8 shows the disposal of the apparatus.

In an embodiment, the collection device 204 is disposed after a single use.

I claim:

1. Apparatus for collecting expelled urine, comprising:
a funnel section opening which diverges to define a first exit and a second exit, said funnel section having a configuration to receive urine and direct said urine to said first exit and to said second exit; and
a receptacle for receiving and storing urine from said first exit, said receptacle including a substantially spherical floatation valve for closing said receptacle when full, such that said receptacle receives an initial flow of urine and subsequent urine is directed to said second exit; wherein
said substantially spherical floatation valve is configured to engage with said first exit so as to block said first exit and prevent subsequent flow into said first exit after receipt of the initial flow of urine; and
said apparatus further comprising a deflector positioned at an entrance to said second exit, said deflector extending across a portion of said second exit so as to cover said portion of said second exit, the deflector being adapted so as to deflect urine towards said first exit in preference to said second exit.

2. The apparatus of claim 1, wherein said receptacle has a screw thread.

3. The apparatus of claim 2, including an extending member configured to engage with said screw thread.

4. The apparatus of claim 1, wherein said receptacle is substantially cylindrical.

5. The apparatus of claim 1, wherein said valve comprises a ball configured to float in urine contained within said receptacle.

6. The apparatus of claim 5, wherein said ball is hollow.

7. The apparatus of claim 1, fabricated from a plastics material by a molding process to facilitate disposal after a single use.

8. Apparatus for collecting a urine sample, comprising:
a funnel opening for receiving expelled urine, said funnel opening diverges to define a first exit and a second exit; and
a deflector positioned at an entrance to said second exit, said deflector extending across a portion of said second exit so as to cover said portion of said second exit, the deflector being adapted so as to deflect urine towards said first exit in preference to said second exit; wherein
said first exit having a configuration to direct received urine towards a collection receptacle, wherein said collection receptacle co-operates with a substantially spherical flotation valve to close off said receptacle after being filled with an initial flow; and
said second exit being adapted to expel excess urine after said receptacle has been filled.

9. The apparatus of claim 8, wherein said substantially spherical floatation valve includes a floating device.

10. The apparatus of claim 9, wherein said floating device is hollow.

11. A method of receiving a sample of urine, comprising the steps of:
placing a substantially spherical floatation valve in a receptacle;
attaching said receptacle to a first exit of a collection device, said collection device having a funnel opening and a second exit, said funnel opening diverges to define said first exit and said second exit;
directing expelled urine towards said first exit by a deflector positioned at an entrance to said second exit, said deflector extending across a portion of said second exit, so as to cover said portion of said second exit such that an initial flow is directed to said receptacle via said first exit until said valve closes;
engaging said substantially spherical floatation valve with said first exit to block said first exit; and
directing subsequent flow to said second exit.

12. The method of claim 11, wherein said receptacle is substantially cylindrical and said floatation valve rises up said receptacle as the receptacle fills with urine.

13. The method of claim 11, wherein said receptacle is attached by a screwing operation.

14. The method of claim 13, wherein said receptacle is unscrewed after use, such that said receptacle is able to be sealed and labeled.

15. The method of 11, including the step of disposing of said collection device after a single use.

\* \* \* \* \*